(12) United States Patent
Bague et al.

(10) Patent No.: US 8,298,568 B2
(45) Date of Patent: Oct. 30, 2012

(54) OIL-IN-WATER TYPE EMULSION WITH LOW CONCENTRATION OF CATIONIC AGENT AND POSITIVE ZETA POTENTIAL

(75) Inventors: Séverine Bague, Marcoussis (FR); Betty Philips, Antony (FR); Jean-Sébastien Garrigue, Verrieres le Buisson (FR); Laura Rabinovich-Guilatt, Paris (FR); Gregory Lambert, Malabry (FR)

(73) Assignee: Novagali Pharma SA, Evry (FR)

( * ) Notice: Subject to any disclaimer, the term of this patent is extended or adjusted under 35 U.S.C. 154(b) by 1080 days.

(21) Appl. No.: 10/991,346

(22) Filed: Nov. 18, 2004

(65) Prior Publication Data
US 2006/0100288 A1 May 11, 2006

(30) Foreign Application Priority Data
Nov. 9, 2004 (EP) .................................... 04292645

(51) Int. Cl.
A61K 9/14 (2006.01)
A61F 2/00 (2006.01)
C07C 231/00 (2006.01)

(52) U.S. Cl. ............ 424/427; 424/489; 514/954; 554/52
(58) Field of Classification Search .................. None
See application file for complete search history.

(56) References Cited

U.S. PATENT DOCUMENTS

| | | | | |
|---|---|---|---|---|
| 5,496,811 A | * | 3/1996 | Aviv et al. | 514/78 |
| 5,588,559 A | * | 12/1996 | Vallet Mas et al. | 222/92 |
| 6,007,826 A | | 12/1999 | Benita et al. | 424/401 |
| 2003/0165545 A1 | * | 9/2003 | Huth et al. | 424/400 |
| 2005/0059583 A1 | * | 3/2005 | Acheampong et al. | 514/11 |
| 2006/0257426 A1 | * | 11/2006 | Baker et al. | 424/204.1 |

FOREIGN PATENT DOCUMENTS

| | | |
|---|---|---|
| EP | 0 696 452 | 2/1996 |
| WO | WO 03/053405 | 7/2003 |

OTHER PUBLICATIONS

Nielloud et al., Drugs and the Pharmaceutical Sciences, Pharmaceutical Emulsions and Suspensions, Marcel Dekker, Inc., vol. 105, 2000, pp. 6-7.*
Benzyl Dimethyl Hexadecyl Ammonium Chloride, poroduct indentification, synonyms, [online Aug. 13, 2010], Retrieved from URL:<http://chemicalland21.com/specialtychem/perchem/BENZYL%20DIMETHYL%20HEXADECYL%20AMMONIUM%20CHLORIDE.htm>.*
Choi, W. et al, "Low toxicity of cationic lipid-based emulsion for gene transfer," Biomaterials, vol. 25, No. 27, Feb. 25, 2004, pp. 5893-5903.
Ott, G. et al, "A cationic sub-micron emulsion (MF59/DOTAP) is an effective delivery system for DNA vaccines," Journal of Controlled Release, vol. 79, No. 1-3, Feb. 19, 2002, pp. 1-5.
Ogawa, S. et al, "Production and Characterization of O/W Emulsions Containing Cationic Droplets Stabilized by Lecithin-Chitosan Membranes," J. Agric. Food Chem., vol. 51, No. 9, Apr. 23, 2003, pp. 2806-2812.
Tamilvanan, S. et al, "The potential of lipid emulsion for ocular delivery of lipophilic drugs," European Journal of Pharmaceutics and Biopharmaceutics, vol. 58, No. 1, Jun. 1, 2004, pp. 357-368.

\* cited by examiner

*Primary Examiner* — Lezah Roberts
*Assistant Examiner* — Nannette Holloman
(74) *Attorney, Agent, or Firm* — Young & Thompson

(57) ABSTRACT

A well tolerated oil-in-water emulsion useful as a delivery vehicle of hydrophobic ingredients such as pharmaceutical drugs, wherein the emulsion particles have a net positive charge and comprises 0.001 to 0.1% of a cationic agent, 0 to 1% of a non ionic surfactant and 0 to 0.5% of an anionic surfactant.

8 Claims, No Drawings

OIL-IN-WATER TYPE EMULSION WITH LOW CONCENTRATION OF CATIONIC AGENT AND POSITIVE ZETA POTENTIAL

The present invention concerns oil-in-water type emulsions useful as delivery vehicle for the administration of lipophilic substances such as pharmaceutical agents. The emulsions of the present invention comprise colloid particles, which are positively charged.

Good ocular tolerability is essential in the design of new ophthalmic products. Hydrophobic therapeutic agents must be formulated in appropriated vehicles such oils, which are not always compatible with ocular administration because of stability or comfort concerns. It is possible to minimize problems related to unpleasant sensations and syndrome exacerbation by reducing the oil content and dispersing the oil phase in a water phase, resulting in an emulsion.

In recent years, oil-in-water type emulsions, in particularly such in which the droplets are of a submicron size (hereinafter "submicron emulsions") gained increasing importance as vehicles for delivery of hydrophobic drugs.

One of the approaches to stabilize an emulsion is by conferring an electrostatic charge to the droplet surface which will result in droplet repulsion and less droplet coalescence. Depending on the nature of the film substances, the external surface of the colloid particles may be charged. Colloidal particles dispersed in a solution are electrically changed due to their ionic characteristics and dipole attributes. This charge, which can be negative resulting in anionic emulsions or positive producing cationic emulsions (Klang et al., Pharm. Dev. Technology 2000, 5, 521-532) is known in the art as the "zeta potential" and is a measure of the magnitude of the repulsion or attraction between particles.

Formulations of submicron emulsions reported in the literature are usually based on a combination of lecithins which are mixtures of phospholipids of various compositions obtained from natural sources, non-ionic or ionic surfactants and of oil such as vegetable oil. Lecithins generally comprise phosphatidylcholine as the major component, which is a zwitterion that is neutral over a wide pH range, and negatively charged phospholipids such as phosphatidylethanolamine, phosphatidylserine and phosphatidic acid. As a consequence of their composition, the colloid particles in most emulsions available were negatively charged. Addition of enough amounts of cationic agents such as stearylamine, oleylamine, chitosan, [N-(1-(2,3-dioleoyloxy)propyl]-N,N,N-trimethylammonium (DOTAP) or others can reverse this surface charge and produce a positively-charged colloid, as reflected by their zeta potential (Rabinovich-Guilatt et al., Chem Phys Lipids 2004, 131:1-13; Liu et al., Pharm. Res. 1996, 13:1856-1860, Klang et al., Int. J. Pharm. 1996, 132:33-44).

In all phospholipid-containing colloids (e.g. liposomes or emulsions), a significant decrease in zeta potential is observed over time, as the result of the additional negative charges brought by free fatty acids (Zuidam and Crommelin, J. Pharm. Sci. 1995, 84:1113-1119). These free fatty acids are thought to be originated from the hydrolysis of the phospholipid molecules into lysophospholipids (Zuidam and Crommelin, J Pharm Sci 1995, 84:1113-1119) and can be a source of toxic side effects following administration (Varveri et al., J. Photochem. Photobiol. A 1995, 91:121-124). In cationic phospholipids colloids, the decrease in zeta potential up to neutrality could in addition to the above produce destabilization of the formulation.

In research, cationic emulsions of quaternary alkylammonium in poly(dimethylsiloxane) (PDMS) oil-in-water emulsion have been employed as model systems to study flocculation/coalescence phenomena (Koh et al., J. Colloid Interface Sc. 2000, 227:390-397). Another example is the microemulsions of hexadecyltrimethylammonium bromide (HTAB)/n-butanol/hexadecane/water which were used to study the intramolecular degradation of cephaclor (De Oliveira et al., J. Pharm. Sci. 1997, 86:616-620). An additional case are mineral oil emulsions rendered cationic by the addition of cetyltrimethylammounium bromide (CTAB) which were used to study drugs transport through side-by-side diffusion cells (Chidambaram and Burgess, AAPS Pharm. Sci. 2000, 2:E28) and drug degradation (De Oliveira et al., J. Pharm. Sci. 1997, 86:616-620).

Positive emulsions (1% corn oil, 0.2% lecithin, 100 mM acetic acid and up to 0.04% chitosan) showed an average droplet size of 1 micron and a good stability to thermal stress (Ogawa et al., J. Agric. Food Chem. 2003, 51:2806-28012 and 51:5522-5527). The authors evoked the possible use of such formulations in the food industry. Also in the food industry, Mancuso et al. have studied the oxidative stability of salmon oil-in-water cationic emulsions containing dodecyltrimethylammonium bromide (DTAB) (J. Agric. Food Chem. 1999, 47:4112-4116).

In the medical field, DOTAP-containing cationic emulsions designed for gene transfer were described by Liu et al. (Pharm. Res. 1996, 13:1856-1860), with 0.025% castor oil and 0.075% emulsifier. Yi et al. prepared also positively charged emulsions of 0.8-1.2% DOTAP, 10% soybean oil and other emulsifiers as a gene delivery system (Pharm. Res. 2000, 17:314-320). Other DOTAP emulsions employed as transfection vectors include those described by Kim et al. (Mol. Cells 2000, 10:142-147, Pharm. Res. 2001, 18:54-60 and Int. J. Pharm. 2003, 252:241-252), Ott et al. (J. Control Release 2002; 79:1-5) and Yoo et al. (J. Control Release 2004, 98:179-188). Emulsions for the same purpose were also formulated with cationic derivatives of cholesterol, such as those described by Min et al. (Biomaterials 2005, 26:1063-1070) or Choi et al. (Biomaterials 2004, 25:5893-5903) and with amphiphilic comb-like polymers (Trimaille et al., J. Colloid Interface Sci. 2003, 258:135-145).

Chitosan cationic formulations containing 0.25-1.5% chitosan, 0-1.5% phospholipids, 0-2.5% poloxamer in a castor:soybean oil phase were also formulated by Jumaa and co-workers (Int. J. Pharm. 1999, 183:175-84). Only the formulation containing poloxamer with chitosan displayed good stability during autoclaving, while the coexistence of chitosan and phospholipids resulted in a destabilization of the emulsion during sterilization. According to the authors, the interaction between the positively charged chitosan with negatively-charged phospholipids which resulted in a damaged emulsifier film around the oil droplets provoked the coalescence of the droplets. These emulsions were evaluated further for their antimicrobial activity for mucosal or parenteral administration (Eur. J. Pharm. Biopharm. 2002, 53:115-23).

None of the above mentioned publications discloses the potential of cationic emulsions of such composition in the ophthalmology domain.

U.S. Pat. No. 5,981,607 discloses an eye drop composition for alleviation of dry eye related symptoms in dry eye patients and contact lens wearers including an emulsion of a higher fatty acid glyceride, polysorbate 80 and Pemulen® in water suitable for topical application to ocular tissue.

U.S. Pat. No. 5,578,586 refers to an ocular treatment composition comprising aqueous oil in water emulsion containing a complex phospholipid having a net charge and an oil. U.S. Pat. No. 5,371,108 describes jellified oil in water emulsion for the same purpose.

U.S. Pat. No. 6,541,018 claims a nanoemulsion comprising an oily phase having oil globules with an average size of less than 100 nm.

U.S. Pat. No. 5,698,219 discloses an oil-in-water nanoemulsion useful as an ophthalmic vehicle containing 0.01-5% of an active agent. These formulations are composed of 0.1-10% of oil, 0.1-10% of a water-miscible non-ionic surface active agent, benzalkonium chloride in a maximum amount of 0.01% and, optionally, antioxidants, isotonizing agents, viscosity modifying agents, stabilizers and buffers. It is implicit that benzalkonium chloride acts as a preservative agent.

U.S. Pat. No. 5,496,811 claims an ocular drug delivery vehicle of an oil-in-water submicron emulsion comprising about 0.5 to 50% of an oil, 0.1 to 10% of an emulsifier, 0.05 to 5% of a non-ionic surfactant and an aqueous component, with a mean droplet size of 100-300 nm. Although the droplet charge is not specified, the chemical composition of this emulsion renders it negatively charged.

The chemical composition of most of the emulsions described in the previous examples renders them negatively charged.

U.S. Pat. No. 6,007,826 discloses a cationic oil-in-water emulsion which comprises colloid particles in which a part of the surface active agents or lipids in the interfacial film have positively charged polar groups therefore the colloid particles having a positive zeta potential. The positive charge is due to cationic lipids (0.05-3% by weight) such as $C_{10}$-$C_{14}$ primary alkylamines (disclosed are stearylamine or oleylamine), $C_{10}$-$C_{24}$ primary alkanolamine or a cholesterol ester (disclosed is cholesterol betainate). The interfacial film is formed in addition to the cationic molecule by phospholipids (0.5-3%) and non-ionic surfactants from the group consisting of poloxamers, tyloxapol, polysorbate, and polyoxyethylene fatty acid esters (0.05-3%). The concentration of the oily core is maintained within the 3-20% range.

U.S. Pat. No. 6,656,460 describes method of treating a dry eye condition by administration of an oleylamine or stearylamine cationic emulsion containing 0.1-0.5% phospholipids, 0.5-2% emulsifying agent such as poloxamer and benzalkonium chloride as an antiseptic agent. The disclosed therapeutic agents are cyclosporine, tacrolimus and sirolimus.

Although the disclosed emulsions show a good stability, there is still a need for more stable emulsions The inventors have discovered that, by using specific ratio between the components of the emulsions, they may obtain very stable emulsions.

The present invention provides an oil-in-water type emulsion, which comprises colloid particles having an oily core surrounded by an interfacial film, wherein said interfacial film has an overall positive charge and comprises:
1) 0.001 to 0.1% by weight of a cationic agent,
2) 0 to 1% by weight of a non ionic surfactant, and
3) 0 to 0.5% by weight of an anionic surfactant; with at least one of said non ionic surfactant and of said anionic surfactant being present.

In a best mode, the concentration of the cationic agent is comprised between 0.001 to 0.05% Essential to the present invention is that the emulsion shows tolerability similar to that of a placebo or NaCl 0.9% solution in the intended mode of administration.

In order to have a positive zeta potential, the total charge of the cationic surfactants should be in excess to the total charge of the anionic surfactants.

Examples of anionic surfactants are anionic lipids intended for pharmaceutical such as phospholipids. Examples of phospholipids, which may be used in the emulsions of the invention, are lecithins; Epikuron 120™ (Lucas Meyer, Germany) which is a mixture of about 70% phosphatidylcholine and 12% phosphatidylethanolamine and about 15% other phospholipids; Ovothin 106™ or Ovothin 200™ (Lucas Meyer, phosphatidylcholine, 18% phosphatidylethanolamine and 12% other phospholipids; a purified phospholipid mixture, e.g. such which is obtained from egg yolk; Lipoid E-80™ (Lipoid AG, Ludwigshafen, Germany) which is a phospholipid mixture comprising about 80% phosphatidylcholine, 8% phosphatidylethanolamine, 3.6% non-polar lipids and about 2% sphingomyeline.

Examples of cationic agents are $C_{10}$-$C_{24}$ primary alkylamines, tertiary aliphatic amines, quaternary ammonium compounds, cationic lipids, amino alcohols, chlorhexidine salts, cationic polymers and the mixture of two or more thereof.

Advantageously, the primary amine is selected from the group consisting of oleylamine and stearylamine; the tertiary aliphatic salt can be dimethyl lauramine or diethanolamine, the amino alcohol can be tris (hydroxymethyl) aminomethane, the chlorhexidine salt can be chlorhexidine dihydrochloride, the cationic polymer can be chitosan, the cationic lipid can be 1,2-dioleyl-3-trimethylammonium-propane, 1,2-dioleoyl-sn-glycero-phosphatidylethanolamine, cationic glycosphingo-lipids or cationic cholesterol derivatives and the quaternary ammonium compound can be selected from the group consisting of benzalkonium chloride, cetrimide, hexadecyltrimethylammonium bromide or chloride, tetracyltrimethylammonium bromide or chloride, dodecyltrimethylammonium bromide or chloride, cetrimonium chloride, benzethonium chloride or bromide, behenalkonium chloride or bromide, cetalkonium chloride or bromide, cetethyldimonium chloride or bromide, cetylpyridinium chloride or bromide, dipalmitoyl hydroxyethylmonium methosulfate, distearyldimonium chloride or bromide, stearalkonium chloride or bromide, myrtrimonium chloride or bromide, benzododecinium chloride or bromide, chlorallyl methenamine, 1-propanaminium, 3-(D-gluconoylamino)-N-(2-hydroxyethyl)-N,N-dimethylchloride and minkamidopropyl dimethyl 2-hydroxyethyl ammonium chloride or bromide and the mixture of two or more thereof.

Examples of non-ionic surfactants which may be included in the emulsion of the invention are tyloxapol, softigen, solutol HS15, poloxamers such as Pluronic F-68LF™ or Lutrol F68, Pluronic L-62LF™ and Pluronic L62D™ (BASF Wyandotte Corp., Parsippany, N.J., USA), polysorbates such as polysorbate 20 and polysorbate 80, polyoxyethylene fatty acid esters such as Emulphor™ (GAF Corp., Wayne, N.J., USA).

Advantageously, the oil-in-water emulsion according to the instant invention comprises benzalkonium chloride as cationic agent and at least tyloxapol as non-ionic surfactant.

The oil phase of the emulsion may comprise one or more members selected from the group consisting of vegetable oils (i.e. soybean oil, olive oil, sesame oil, cotton seed oil, castor oil, sweet almond oil), mineral oil (i.e. petrolatum and liquid paraffin), medium chain triglycerides (MCT) (i.e. a triglyceride oil in which the carbohydrate chain has about 8-12 carbon atoms), oily fatty acid, isopropyl myristate, oily fatty alcohols, esters of sorbitol and fatty acids, oily sucrose esters, and in general any oily substance which is physiologically tolerated.

The major component of the oily phase will generally be either vegetable oil and/or MCT. Fatty acids or fatty alcohols may be included in cases where the hydrophobic substance to be carried by the emulsion is not sufficiently soluble in the oily phase.

Examples of MCT oil which may be used in emulsions of the present invention are TCM™ (Société des Oléagineux, France), Miglyol 812™ (Dynamit Novel, Sweden). Examples of vegetable oil which may be used in emulsions of the present invention are castor oil, soybean oil, cottonseed oil, olive oil and sesame oil.

Advantageously, the concentration of the oily core is not higher than 5% (w/w), preferably about 0.5 to 3% (w/w).

As known, the emulsion may also comprise various additives such as osmotic pressure regulators, e.g. sucrose, glycerine or mannitol; antioxidants, e.g. alpha-tocopherol, sodium bisulfite, sodium metasulfite, sodium thiosulfate anhydrous, citric acid monohydrate, ascorbyl palmitate and ascorbic acid; or preservatives, e.g. thiomersal, chlorobutanol, benzyl alcohol, phenoxyethanol, phenylethyl alcohol, sorbic acid, EDTA and methyl-, ethyl-, or butyl paraben. In some applications, additives may further be included in the substance and, for example, some suitable additives may include dextrose, carriers, stabilizing agents, wetting agents, viscosity enhancers, hydrogels or other similar materials.

According to the invention, concentrations of the ingredients of the emulsion are given as "%", meaning weight of ingredient in hundred weight units of total composition ("w/w").

A preferred pH in the aqueous phase of the emulsion of the invention is 4.0-8.5, 6.0-8.0 being particularly preferred.

It is generally preferred that the particles in the emulsion will have an average particles size of about 0.1 to 1 μm, advantageously of about 300 nanometers, more advantageously between about 100 to 200 nm.

Emulsions in accordance with the present invention may be formulated into pharmaceutical compositions with various hydrophobic active ingredients for a large number of pharmaceutical applications. Also hydrophilic agents can be administered with these emulsions.

The pharmaceutical composition according to the invention may be used for ocular, parenteral or topical administration.

According to the invention, the emulsion may be formulated especially for ocular administration of said active ingredients. In this oil/water emulsion, the water-insoluble drug is solubilized in the internal oil phase, thereby remaining in the preferred solution state. In addition, the blurred vision caused by oils is minimised by the water in the external phase. Furthermore, the concentration of the drug in the oil phase can be adjusted to maximise thermodynamic activity, thus enhancing drug penetration to deeper tissues.

Consequently, the instant invention provides the use of an oil-in-water emulsion according to the instant invention for the preparation of a medicament useful for preventing or treating ophthalmic disorders.

The instant invention also provides a method of treatment of ocular conditions comprising a pharmaceutical composition comprising an oil-in-water type emulsion, which comprises colloid particles having an oily core surrounded by an interfacial film, wherein said interfacial film has an overall positive charge and comprises:

1) 0.001 to 0.1% by weight of a cationic agent,
2) 0 to 1% by weight of a non ionic surfactant, and
3) 0 to 0.5% by weight of an anionic surfactant; with at least one of said non ionic surfactant and of said anionic surfactant being present.

A wide variety of ocular conditions such as glaucoma, ocular inflammation, ocular infections, ocular allergies, ocular infections, cancerous growth, neo vessel growth originating from the cornea, retinal oedema, macular oedema, diabetic retinopathy, retinopathy of prematurity, degenerative diseases of the retina (macular degeneration, retinal dystrophies), retinal diseases associated with glial proliferation may be prevented or treated using the cationic emulsions according to the present invention.

Some substances suitable for delivery to the eye may include, for example, antibiotics (such as tetracycline, chlortetracycline, bacitracin, neomycin, polymyxin, gramicidin, cephalexin, oxytetracycline, chloramphenicol, kanamycin, rifampicin, tobramycin, gentamycin, ciprofloxacin, aminosides, erythromycin and penicillin, quinolone, ceftazidime, vancomycine imipeneme; antifungals such as amphotericin B and miconazole; antibacterials such as sulfonamides, sulfadiazine, sulfacetamide, sulfamethizole and sulfisoxazole, nitrofurazone and sodium propionate; antivirals, such as idoxuridine, trifluorotymidine, acyclovir, ganciclovir, cidofovir and interferon; antibacterial agents such as nitrofurazone and sodium propionate; non-antibiotic, anti-infection, anti-bacterial or anti-microbial drugs such as iodine based preparation triclosan, chlorhexidine; antiallergenics such as sodium cromoglycate, antazoline, methapyriline, chlorpheniramine, cetirizine, pyrilamine and prophenpyridamine; synthetic gluocotticoids and mineralocorticoids and more generally hormones forms derivating from the cholesterol metabolism (DHEA, progesterone, estrogens); anti-inflammatories such as hydrocortisone, hydrocortisone acetate, dexamethasone, dexamethasone 21-phosphate, fluorocinolone, medrysone, prednisolone acetate, luoromethalone, triamcinolone and triamcinolone acetonide and their derivatives; non-steroidal anti-inflammatories such as salicylate, indomethacin, ibuprofen, diclofenac, flurbiprofen and piroxicam and COX2 inhibitors; antineoplastics such as carmustine, cisplatin, mitomycin and fluorouracil; immunological drugs such as vaccines and immune stimulants; insulin, calcitonin, parathyroid hormone and peptide and vasopressin hypothalamus releasing factor; beta adrenergic blockers such as timolol maleate, levobunolol HCl and betaxolol HCl, timolol-base, betaxolol, atenolol, epinephrine, dipivalyl, oxonolol, acetazolamide-base and methazolamide; cytokines, interleukins, prostaglandins (also antiprostaglandins, and prostaglandin precursors) and growth factors (growth factors such as epidermal growth factor, fibroblast growth factor, platelet derived growth factor, transforming growth factor beta, ciliary neurotrophic growth factor, glial derived neurotrophic factor, NGF, EPO, PlGF); antibodies or antibodies fragments, oligoaptamers, aptamers and gene fragments (oligonucleotides, plasmids, ribozymes, small interference RNA, nucleic acid fragments, peptides, antisense sequences); immunomodulators such as cyclosporine, endoxan, sirolimus, tacrolimus, thalidomide, tamoxifene; antithrombolytic and vasodilator agents such as rtPA, urokinase, plasmin, nitric oxide donors.

The drug may be present in an amount of about 0.0001 to 5% by weight of the composition. Depending upon whether the drug is hydrophilic or hydrophobic, it will be physically present in the oily phase or the aqueous component.

The invention is further illustrated by the examples below.

EXAMPLE 1

Preparation of Cationic Emulsions Whereas the Cationic Agent is CTAB

Methods:

| Component | Z01EM042 | Z01EM043 |
|---|---|---|
| CTAB (cationic agent) | 0.05% | 0.1% |
| MCT (oil) | 2% | 2% |
| Alpha tocopherol (antioxidant) | 0.01% | 0.01% |
| Lipoid E80 (anionic surfactant) | 0.32% | 0.32% |
| Lutrol F68 (non ionic surfactant) | 0.5% | 0.5% |
| Glycerin (tonicity agent) | 2.25% | 2.25% |
| Water | 94.87% | 94.82% |

The oily phase components were successively weighed in the same beaker and then magnetically stirred under a slight heating (40° C.) until a yellow, limpid and slightly viscous phase is obtained. Aqueous phase components were successively weighed in the same beaker and then magnetically stirred under a slight heating (40° C.) until a transparent, limpid and fluid phase is obtained. Both phases were heated to 65° C. The coarse emulsion was formed by rapid addition of the aqueous phase in the oily phase and was then rapidly heated to 75° C. The aqueous phase and coarse emulsion beakers were protected by a film to avoid any water evaporation. The emulsion was white and slightly transparent. The emulsion droplet size was then decreased by a 5 minutes high shear mixing with POLYTRON PT 6100. The emulsion became milky. The emulsion temperature was cooled down to 20° C. using an ice bath. The final emulsion was obtained by homogenization in a microfluidizer (C5, Avestin) using continuous cycles for 5 min at a pressure of 10 000 psi. The emulsion was milky, very fluid and did not adhere on the glass. The emulsion temperature was decreased to 25° C. Its pH was measured and then adjusted to 8.00 using a 0.1 M HCl or 0.1 M NaOH solution. Emulsion was conditioned in tinted glass vials with nitrogen bubbling and then sterilized in an autoclave 20 minutes at 121° C.

The mean particle size of the emulsions droplets was determined by quasi-elastic light scattering after dilution in water using a High Performance Particle Sizer (Malvern Instruments, UK). The electrophoretic mobility was measured at 25° C. in a Malvern Zetasizer 2000 (Malvern Instruments, UK) following a 1:200 dilution in double distilled water. The pH was measured with a pH meter (Mettler Toledo).

Results:

| | Z01EM042 | Z01EM043 |
|---|---|---|
| Droplet size (nm) | 126 | 128 |
| Zeta potential (mV) | 36.4 | 49.5 |

EXAMPLE 2

Stability of Cationic Emulsions Whereas the Cationic Agent is CTAB

Methods:
The stability of the autoclaved emulsions (droplet size, zeta potential) at 80° C. was monitored for 14 days.

Results:

| | Z01EM042 | | | Z01EM043 | | |
|---|---|---|---|---|---|---|
| | T0 | 7 d. | 14 d. | T0 | 7 d. | 14 d. |
| Droplet size (nm) | 126 | 143 | 155 | 128 | 140 | 151 |
| Zeta potential (mV) | 36.4 | 39.0 | 38.7 | 49.5 | 53.8 | 49.9 |

The zeta potential of the emulsions presented in this example was more stable than previously known formulations (data not shown).

EXAMPLE 3

Preparation of a Cationic Emulsion Whereas the Cationic Agent is Benzalkonium Chloride Methods:

| Component | Z01EM096 | ZO1EM089 |
|---|---|---|
| Benzalkonium chloride (cationic agent) | 0.1% | 0.02% |
| MCT (oil) | 2% | 2% |
| Alpha tocopherol (antioxidant) | 0.01% | 0.01% |
| Lipoid E80 (anionic surfactant) | 0.32% | — |
| Tyloxapol (anionic surfactant) | — | 0.32% |
| Lutrol F68 (non ionic surfactant) | 0.5% | 0.5% |
| Glycerin (tonicity agent) | 2.25% | 2.25% |
| Water | 94.82% | 94.90% |

Preparation description: as described previously.

Results:

| | Z01EM096 | ZO1EM089 |
|---|---|---|
| pH | 5.98 | 6.28 |
| Zeta potential (mV) | 44.0 | 33.7 |

EXAMPLE 4

Stability of a Cationic Emulsion Whereas the Cationic Agent is Benzalkonium Chloride The stability of the autoclaved emulsion (pH, zeta potential) at 80° C. was monitored for 15 days.

Results:

| | Z01EM096 | |
|---|---|---|
| | T0 | T15 |
| pH | 5.98 | 4.09 |
| Zeta potential (mV) | 44.0 | 29.3 |

The zeta potential of the emulsion presented in this example was more stable than previously known formulations (data not shown).

EXAMPLE 5

Preparation of a Cationic Emulsion Whereas the Cationic Agent is Benzalkonium Chloride Methods:

| Component | Z01EM093 |
|---|---|
| Benzalkonium chloride (cationic agent) | 0.02% |
| MCT (oil) | 1% |
| Alpha tocopherol (antioxidant) | 0.005% |
| Tyloxapol (non ionic surfactant) | 0.16% |
| Lutrol F68 (non ionic surfactant) | 0.5% |
| Glycerin (tonicity agent) | 2.25% |
| Water | 96.07% |

Preparation description: as described previously.

Results:

| | Z01EM093 |
|---|---|
| pH | 7.31 |
| Zeta potential (mV) | 20.4 |

EXAMPLE 6

Stability of a Cationic Emulsion Whereas the Cationic Agent is Benzalkonium Chloride The stability of the autoclaved emulsion (pH, zeta potential) at 80° C. was monitored for 15 days.

Results:

| | Z01EM093 | |
|---|---|---|
| | T0 | T14 |
| pH | 7.31 | 5.59 |
| Zeta potential (mV) | 20.4 | 21.3 |

The zeta potential of the emulsion presented in this example was more stable than previously known formulations (data not shown).

EXAMPLE 7

Example of Cationic Emulsions Whereas The Interfacial Film Comprises a Cationic Agent and a Non-Ionic Surfactant (Without Phospholipids) or Phospholipids Methods:

| Component | Z01EM018 | Z01EM008 | Z01EM012 | Z01EM009 | Z01EM014 |
|---|---|---|---|---|---|
| MCT (oil) | | | 2 | | |
| Tyloxapol (non ionic surfactant) | — | 0.32 | 0.2 | — | — |
| Solutol (non ionic surfactant) | — | — | — | 0.32 | 0.2 |
| Lipoid E80 (anionic surfactant) | 0.32 | — | — | — | — |
| Oleylamine (cationic agent) | | | 0.1 | | |
| Alpha tocopherol (antioxidant) | | | 0.01 | | |
| Lutrol F68 (non ionic surfactant) | | | 0.5 | | |
| Glycerin (tonicity agent) | | | 2.25 | | |
| Water | | | up to 100 | | |

Preparation: as described previously.

Results:

| | Z01EM018 | Z01EM008 | Z01EM012 | Z01EM009 | Z01EM014 |
|---|---|---|---|---|---|
| Droplet size (nm) | 162 | 176 | 169 | 186 | 179 |
| Zeta potential (mV) | 60.3 | 51.0 | 56.0 | 57.7 | 57.6 |
| pH | 6.95 | 7.23 | 7.24 | 7.31 | 7.29 |

ND: Not determined

EXAMPLE 8

Stability of Cationic Emulsions Whereas the Interfacial Film Comprises a Cationic Agent and a Non-Ionic Surfactant (Without Phospholipids) Compared to a Phospholipids-Containing Emulsion The stability of the autoclaved emulsions (droplet size, zeta potential) at 80° C. was monitored for 15 days.

|  | Time | Z01EM018 | Z01EM008 | Z01EM012 | Z01EM009 | Z01EM014 |
|---|---|---|---|---|---|---|
| Droplet size (nm) | 0 | 162 | 176 | 169 | 186 | 179 |
|  | 15 days | 170 | 193 | 199 | 198 | 204 |
| Zeta potential (mV) | 0 | 60.3 | 51.0 | 56.0 | 57.7 | 57.6 |
|  | 15 days | −24.0 | 27.5 | 33.4 | 29.7 | 23.0 |
| pH | 0 | 6.95 | 7.23 | 7.24 | 7.31 | 7.29 |
|  | 15 days | 4.35 | 5.41 | 5.07 | 4.95 | 4.87 |

EXAMPLE 9

Cationic Emulsions Whereas the Interfacial Film Comprises Solely the Cationic Agent and One Non-Ionic Tensioactive Agent Methods:

| Component | Z01EM024 |
|---|---|
| Oleylamine (cationic agent) | 0.1 |
| MCT (oil) | 2 |
| Alpha tocopherol (antioxidant) | 0.01 |
| Lutrol F68 (surfactant) | 0.5 |
| Glycerine (tonicity agent) | 2.25 |
| Water | 95.14 |

Preparation: as described previously.
Results:

|  | Z01EM024 |
|---|---|
| Droplet size (nm) | 176 |
| Zeta potential (mV) | 60.1 |

EXAMPLE 10

Cationic Emulsions Whereas the Interfacial Film Comprises a Cationic Agent and a Combination of Non-Ionic Surfactant and Phospholipids Methods:

| Component | Z01EM048 | Z01EM051 | Z01EM054 |
|---|---|---|---|
| MCT |  | 2 |  |
| Lipoid E80 | 0.15 | 0.1 | 0.05 |
| Tyloxapol | 0.15 | 0.1 | 0.05 |
| Oleylamine |  | 0.1 |  |
| α-tocopherol |  | 0.01 |  |
| Lutrol F68 |  | 0.5 |  |
| Glycerine |  | 2.25 |  |
| Water |  | Up to 100 |  |

Preparation: as described previously.

Results:

| Component | Z01EM048 | Z01EM051 | Z01EM054 |
|---|---|---|---|
| Droplet size (nm) | 146 | 146 | 156 |
| Zeta potential (mV) | 53.1 | 55.3 | 56.3 |

EXAMPLE 11

Stability of Cationic Emulsions Whereas the Interfacial Film Comprises a Cationic Agent and a Combination of Non-Ionic Surfactant and Phospholipids Methods:
The stability of the autoclaved emulsions (droplet size, zeta potential) at 80° C. was monitored for 14 days.
Results:

|  | Time | Z01EM048 | Z01EM051 | Z01EM054 |
|---|---|---|---|---|
| Droplet size (nm) | T0 | 146 | 146 | 156 |
|  | 7 | 163 | 159 | 178 |
|  | 14 | 173 | 169 | 178 |
| Zeta potential (mV) | T0 | 53.1 | 55.3 | 56.3 |
|  | 7 | 30.3 | 27.5 | 25.2 |
|  | 14 | 21.6 | 10.7 | 22.5 |

ND: not determined

EXAMPLE 12

Cationic Emulsions Whereas the Intarfacial Film Comprises a Cationic Agent and a Combination of Non-Ionic Surfactant and Phospholipids Methods:

| Component | Z01EM057 | Z01EM060 | Z01EM063 |
|---|---|---|---|
| MCT |  | 2 |  |
| Lipoid E80 | 0.15 | 0.1 | 0.05 |
| Solutol HS | 0.15 | 0.1 | 0.05 |
| Oleylamine |  | 0.1 |  |
| α-tocopherol |  | 0.01 |  |
| Lutrol F68 |  | 0.5 |  |
| Glycerine |  | 2.25 |  |
| Water |  | Up to 100 |  |

Preparation: as described previously.

Results:

| Component | Z01EM057 | Z01EM060 | Z01EM063 |
|---|---|---|---|
| Droplet size (nm) | 149 | 158 | 160 |
| Zeta potential (mV) | 56.0 | 57.5 | 55.7 |

EXAMPLE 13

Stability of Cationic Emulsions Whereas the Interfacial Film Comprises a Cationic Agent and a Combination of Non-Ionic Surfactant and Phospholipids Methods:
The stability of the autoclaved emulsions (droplet size, zeta potential) at 80° C. was monitored for 14 days.
Results:

| | Time | Z01EM057 | Z01EM060 | Z01EM063 |
|---|---|---|---|---|
| Droplet size (nm) | T0 | 149 | 158 | 160 |
| | 7 d. | 163 | 175 | 184 |
| | 14 d. | 172 | 185 | 193 |
| Zeta potential (mV) | T0 | 56.0 | 57.5 | 55.7 |
| | 7 d. | 34.6 | 33.2 | 27.2 |
| | 14 d. | 5.9 | 4.4 | 6.8 |

EXAMPLE 14

Ocular Tolerability Test after Subchronic Topical Administration

Methods:
The subchronic topical tolerability of the new emulsions was evaluated in vivo in male New Zealand albino rabbits, 9 to 10 week-old. One hundred uL of each emulsion were instilled in the left eye of the animals, twice a day for a 5-days period (10 instillations). Macroscopic ocular reactions (discomfort, discharge, redness chemosis and corneal opacity) were evaluated daily and compared to saline.
Evaluated compositions:

| Z01EM021 | Z01EM022 |
|---|---|
| | MCT 2% |
| Tyloxapol 0.05% | Solutol HS 0.05% |
| OA 0.1% | |
| Vitamin E 0.01% | |
| Pluronic F68 0.5% | |
| Glycerol 2.25% | |
| Water up to 100% | |

Results:
The new formulations were well tolerated.

EXAMPLE 15

Ocular Tolerability Test after Chronic Topical Administration

The aim of this study was to determine the ocular tolerance of a cationic emulsion (Z01EM018, see composition in previous examples) after multiple daily ocular topical administrations for 28 consecutive days into the right eye of albino rabbits.
Methods:
Thirty New Zealand White rabbits were randomly divided into three groups of ten animals. The rabbits of Group 1 and 2 received four or eight daily ocular instillations (50 microlitres) of Z01EM018 in the right eye for 28 days. The rabbits in the Group 3 received eight daily ocular instillations (50 microlitres) of 0.9% NaCl for 28 days and served as controls. The general tolerability (body weight, food and water consumptions, general aspect and behaviour) and the ocular tolerability (observations of the eyes with an ophthalmoscope and with a slit-lamp) were conducted periodically. On Day 29, animals were euthanized, necropsied and eyes and ocular adnexa were microscopically examined.
Results:
Multiple daily (4× or 8×/day) ocular instillations with Z01EM018 produced no effects on body weights and food and water consumptions, as well as organ weights and macroscopic observations at necropsy.
Ocular reactions were confined to slight conjunctival redness in both treated and untreated eyes. Similar ocular reactions were observed in the rabbits that received 8 daily instillations of NaCl 0.9%. Microscopic examination only showed slight signs of irritation probably due to the repeated instillations.

The invention claimed is:

1. An oil-in-water emulsion, comprising:
   colloid particles having an oily core surrounded by an interfacial film;
   said interfacial film having an overall positive charge and comprising, based on total emulsion weight:
   1) 0.001 to 0.05% by weight of a cationic agent, said cationic agent being cetalkonium chloride,
   2) a non ionic surfactant, said nonionic surfactant being present in an amount up to 1% by weight and consisting of tyloxapol and poloxamer, and
   3) 0% by weight of phospholipids; and
   said oil core being not higher than 5% weight.

2. The oil-in-water emulsion according to claim 1, wherein the concentration of the oily core is about 0.5 to 3% w/w.

3. The oil-in-water emulsion according to claim 1, wherein said colloidal particles have an average particle size of about 0.1 to 1 μm.

4. The oil-in-water emulsion according to claim 3, wherein said colloidal particles have an average particle size of about 300 nm.

5. The oil-in-water emulsion according to claim 3, wherein said colloidal particles have an average particle size of about 100 to 200 nm.

6. A pharmaceutical composition comprising a pharmaceutically effective amount of a well tolerated carrier with an active ingredient, said carrier being an oil-in-water emulsion according to claim 1.

7. The pharmaceutical composition according to claim 6, wherein said composition is an ophthalmic preparation.

8. The pharmaceutical composition according to claim 6, wherein the active ingredient is sirolimus.

* * * * *